(12) United States Patent
Alam et al.

(10) Patent No.: US 6,558,940 B2
(45) Date of Patent: May 6, 2003

(54) STREPTOMYCES STRAIN WITH POTENTIAL ANTI-MICROBIAL ACTIVITY AGAINST PHYTOPATHOGENIC FUNGI

(75) Inventors: Mansoor Alam, Lucknow (IN); Abdul Sattar, Lucknow (IN); Sushil Kumar, Lucknow (IN); Abdul Samad, Lucknow (IN); Om Prakash Dhawan, Lucknow (IN); Suman Preet Singh Khanuja, Lucknow (IN); Ajit Kumar Shasany, Lucknow (IN); Seema Singh, Lucknow (IN); Poovappallivadakethil Viswanathan Nair Ajaya Kumar, Lucknow (IN); Abdul Khaliq, Lucknow (IN); Mohammad Zaim, Lucknow (IN); Saba Shahabuddin, Lucknow (IN); Mala Trivedi, Lucknow (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/538,456

(22) Filed: Mar. 30, 2000

(65) Prior Publication Data

US 2002/0076802 A1 Jun. 20, 2002

(51) Int. Cl.$^7$ .............................. C12N 1/00; C12N 1/12; C12N 1/20
(52) U.S. Cl. ................ 435/243; 435/252.1; 435/252.35; 435/253.5
(58) Field of Search ........................... 435/252.1, 253.5, 435/252.35

(56) References Cited

U.S. PATENT DOCUMENTS

| | | | | |
|---|---|---|---|---|
| 5,403,584 A | * | 4/1995 | Crawford et al. | 424/93.43 |
| 5,527,526 A | * | 6/1996 | Crawford | 424/93.43 |
| 5,968,503 A | * | 10/1999 | Crawford | 424/93.43 |
| 6,193,964 B1 | * | 2/2001 | Shiang et al. | 424/122 |

* cited by examiner

Primary Examiner—David Gozo
Assistant Examiner—David A. Lambertson
(74) Attorney, Agent, or Firm—Powell, Goldstein, Frazer & Murphy, LLP (57) ABSTRACT

The present invention relates to a new strain of Streptomyces sp., called CIMAP A$_1$ isolated from the soil of geranium (*Pelargonium graveolens*) planted in the experimental fields of CIMAP and having the accession No. ATCC PTA-4131 and capable of inhibiting the growth of phytopathogenic fungi.

4 Claims, 5 Drawing Sheets (3 of 5 Drawing Sheet(s) Filed in Color)

M : λ Hind III + EcoRI digest

MAP primers

| Primers | Nucleotide Sequence |
|---|---|
| 1. MAP 04 | 5' TGC GCG ATC G 3' |
| 2. MAP 05 | 5' AAC GTA CGC G 3' |
| 3. MAP 06 | 5' GCA CGC CGG A 3' |
| 4. MAP 09 | 5' CGG GAT CCG C 3' |
| 5. MAP 12 | 5' CCA AGC TTG C 3' |
| 6. MAP 15 | 5' AAG ATA GCG G 3' |
| 7. MAP 16 | 5' GGA TCT GAA C 3' |
| 8. MAP 17 | 5' TTG TCT CAG G 3' |
| 9. MAP 19 | 5' GGA CTC CAC G 3' |
| 10. MAP 20 | 5' AGC CTG ACG C 3' |

(MAP - Medicinal and Aromatic plants)

STREPTOMYCES STRAIN WITH POTENTIAL ANTI-MICROBIAL ACTIVITY AGAINST PHYTOPATHOGENIC FUNGI

FIELD OF THE INVENTION

The present invention relates to a new strain of Streptomyces isolated from the soil of geranium (*Pelargonium graveolens*) at Central Institute of Medicinal and Aeromatic Plants (CIMAP), Lucknow, India—the newly isolated strain Streptomyces CIMAP-A$_1$ is capable of inhibiting the growth of a wide range of phytopathogenic fungi and has been found to be highly effective in protecting rose-scented geranium from anthracnose disease caused by *Colletotrichum acutatum* and opium poppy from damping-off caused by *Pythium dissotocum*. The said novel strain of Streptomyces has been isolated from a soil at CIMAP, where field experiments in respect of the plant *Pelargonium graveolens* were conducted.

BACKGROUND OF THE INVENTION

Fungal phytopathogenes cause considerable damage to the medicinal and aromatic plants. These pathogens produce various kinds of diseases whose occurrence in severe form may either kill emerging seedlings or reduce plant growth and adversely effect crop yield. Various phytopathogenic fungi including Rhizoctonia, Sclerotinia, Pythium, Fusarium, Curvularia, Alternaria, Collectotrichum and Thielavia cause different types of diseases on medicinal and aromatic plants such as stem rot and twig blight (*Sclerotinia sclerotiorum*) on periwinkle, Egyptian henbane, and ammi majus; leaf blight (*Curvularia andropogonis*); lethal yellowing (*Pythium aphanidermatum*) and collar rot (*Fusarium moniliforme*) on Java citronella; damping-off (*Pythium dissotocum*), collar rot (*Rhizoctonia solani*) and leaf blight (*Alternaria alternata*) opium poppy, stolon and root rot (*Thielavia basicola*) on mints and anthracnose disease *Colletotrichum acutatum* on geranium. (Alam et al 1983, Indian Phytopath. 367: 480–483, ibid 1992 Plant 43:10578–1061; ibid 1996 Indian Phytopath. 49:94–97; Sattar et al 1993, Indian J. Plant Pathol 10: 10–11; ibid 1999, Indian J. Plant Pathol 17:74–76).

Chemical pesticides are commonly used to protect plants from the fungal infections but their intensive and indiscriminate uses pose many serious problems such as development of resistant strains of the pathogen, build up of harmful residues in the plant parts, non-target effect on beneficial microflora and environmental pollution. Thus, to avoid such problems. attention has been focused to use microorganisms such as fungi, bacteria and actinomycetes as biocontrol agents to minimize infection caused by plant pathogens.

Streptomyces spp. are commonly distributed in the soil rhizosphere and phyllosphere by which they produce strong antagonistic effect on the fungal phytopathogens and protect plants from the attack of the pathogens (Broadbent et al 1971, Aust. J. Biol. Sci 24: 925–944, Lahdenpera 1987, Acta Horticulture 216: 85–92, El-Abyad et al 1993. Plant and Soil, 149 185–195). *Streptomyces griseoviridis* isolated from Finnish sphagnum peat produce strong antagonistic effect on the growth of *Fusarium culmorum, Pythium debaryanum* and *Rhizoctonia solani* and its spraying reduce the damage caused by them (Tahvonen, 1985, Vaxskyddsnotiser 49 86–90, White el al. 1998, In Brighton Crop Protection Conference on Pests and Diseases vol 1: 221–226). A direct evidence that the antibiotic geldamycin produced by *Streptomyces hygroscopius* var. *geldanus* suppressed the growth of *Rhizoctonia solani*, thus controlled Rhizoctonia root rot of pea (Rothrock and Gottlieb, 1984, Can. J. Microbiol 30: 1440–1447). Several Streptomyces cultures have been isolated from the soil of CIMAP experimental fields at Lucknow and they have been maintained in our culture collection. One of the isolates of Streptomyces i.e. Streptomyces CIMAP-A$_1$ shows strong antagonistic activities against the wide range of fungal phytopathogens in vitro. One of the most recent and taxonomic studies of Streptomyces was carried out in the International Streptomyces Project (I.S.P) where more than 400 type strains were examined independently by Standardized procedure (Shirling E B and Gottlieb D. 1968, International Journal of Systematic Bacteriology, 18: 69–186, 279–31; Ibid. 1961 International Journal of Systematic Bacteriology 22: 265–394). Streptomyces species were assigned to seven color series i.e. blue, green, gray, red, violet, white and yellow (Pridham and Tesener, 1974, Family VII Streptomyectaceae Waksman and Henriei, 1943. IN Bergey's Mannual of Determinative Bacteriology, 8$^{th}$ edn., ed Buchman, R E & Cibbon, N. E. pp.747–845 Baltimore; Willams & Wilkins). Subsequently, the color series were extended to accommodate additional colors. The distinctive morphology of the sporing structures have been widely used in the characterization of Streptomyces species. The spore chain morphology determined by light microscopy and spore surface ornament determined by electronic microscopy have been considered important in many classifications. (Etlinger et al 1958, Archive fur Mikrobiologie 31,326–358, Waksman S. A. 1961, The Actinomycestes Vol.2. Classification, Identification and Description of General and Species, Baltimore: Williams and Willins, Hutter, R. 1967. Systematik de Steptomyceten. Basel & New York S Karger).

Streptomyces spp. are morphologically characterized by the production of highly branched substrate mycelium (rarely bearing spores) that further form a network of white aerial hyphae bearing spores in chain at the tip of sporogenous filament (Kustner, E, 1961; International Bulletin of Bacteriological Nomenclature and Taxonomy 11, 91–98).

OBJECT OF THE INVENTION

The main object of the present invention relates to a novel strain of Streptomyces spp. (CIMAP A$_1$) having potential antifungal activities and capable of reducing infection by fungal pathogens.

An another object of the invention is to use the newly isolated strain of Streptomyces spp. (CIMAP A$_1$) for the control of different diseases like damping off disease of opium poppy and anthracnose disease of rose scented geranium by application in a suitable medium.

SUMMARY OF THE INVENTION

The invention provides a novel Streptomyces sp. capable of inhibiting the growth of a wide range of phytopathogenic fungi.

The strain deposited at the American Type Culture Collection (ATCC), Manassas, Va. on Mar. 12, 2002, and assigned to Accession Number PTA-4131.

DETAILED DESCRIPTION OF THE INVENTION

The present invention pertains to the isolation of a number of actinomycetes from the soil and identification of a new Streptomyces strain referred to as Streptomyces CIMAP-A$_1$. The stain is deposited at American Type Culture Collection (ATCC), Manassas, Va, on Mar. 12, 2002, and assigned to Accession Number PTA-4131. This strain is shown to exhibit strong antagonism towards a wide range of fungal phytopathogens that cause various kinds of diseases such as damping-off, root rot, stem rot, collar rot, twig blight, lethal yellowing, leaf blight and anthracnose as shown in Table 1. As such, this Streptomyces strain is suitable as biocontrol agent that can be used to protect plants against infection by these phytopathogens. Thus, Streptomyces CIMAP-$A_1$ is useful in methods for reducing the susceptibility of plant to fungi infection.

Accordingly, the novel strain of Streptomyces, Streptomyces CIMAP-$A_1$, has been found to inhibit growth of Streptomyces sp. and *Botrytis cincrea* by more than 90%, of *Sclerotinia sclerotiorum* by more than 85%, of Curvularia spp by more than 80%, of Alternaria spp by more than 65% of *Corynespora cassiicola* by more than 64% of *Thielavia basicola* by more than 54% of *Rhizoctonia solani* by more than 20% of Pythium spp by more than 20% and of Fusarium spp by more than 25% in vitro. The invention further provides information on the characterization of the strain Streptomyces CIMAP-$A_1$ which initially produce smooth and dull white colonies on PDA which later form discrete lichnoid colonies. In the later stages of growth, it produces a weft of aerial mycelium and turn into dark brown in color and the aerial mycelium at maturity form chain of spiral spores called orthrospores. Since species delineation within the genus Streptomyces is difficult and it requires a large amount of chemotaxonomic and molecular tests, the applicants designate the strain as Streptomyces CIMAP-$A_1$.

Accordingly, the invention provides a biologically pure culture of Streptomyces sp., CIMAP $A_1$ strain bearing accession No. ATCC PTA-4131 and capable of inhibiting the growth of phytopathogenic fungi.

Another embodiment of the invention provides a new stain of Streptomyces sp., called CIMAP $A_1$ isolated from the soil of geranium (*Pelargonium graveolens*) planted in the experimental fields of CIMAP and having the accession No. ATCC PTA-4131 and capable of inhibiting the growth of phytopathogenic fungi.

Figure 1A:
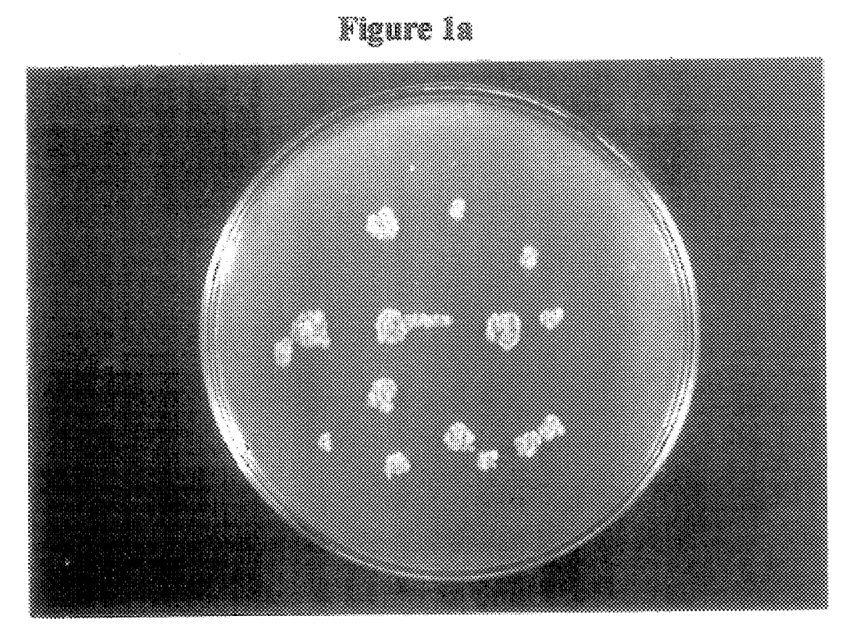
FIG. 1a. shows cultural characteristic of Streptomyces CIMAP $A_1$ strain. It is clear from FIG. 1 that the isolate Streptomyces CIMAP $A_1$ initially produce smooth and dull white colonies on PDA which later form discrete and lichnoid colonies.
Figure 1B:
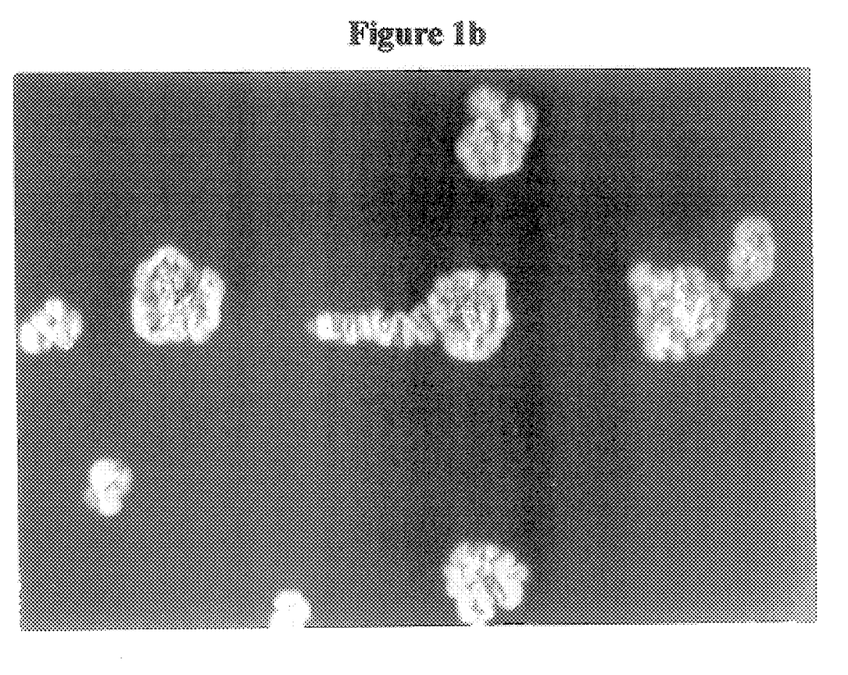
FIG. 1b. shows the enlarged view (a close-up view) of colonies characteristic of Streptomyces CIMAP $A_1$ strain.
Figure 2:
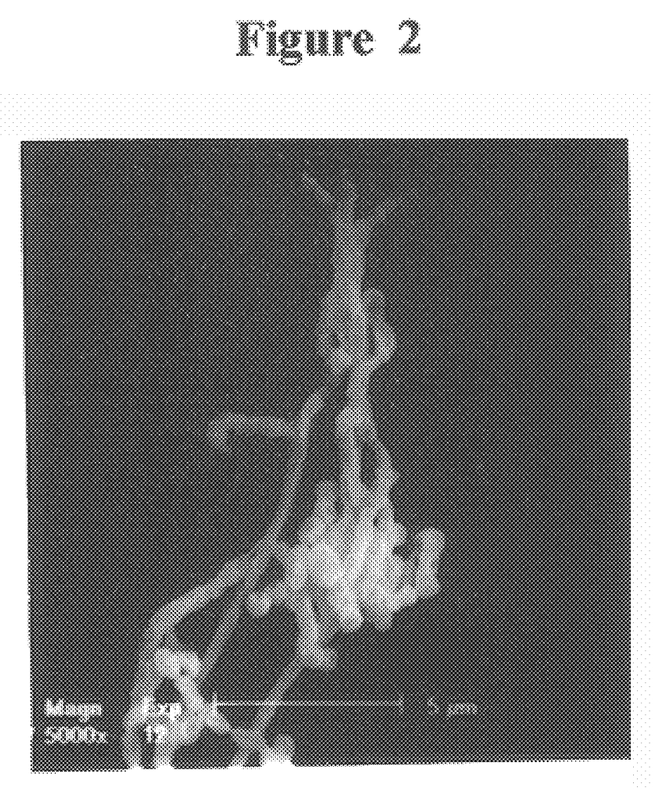
FIG. 2. shows electron photomicrograph of Streptomyces CIMAP-$A_1$ strain.
Figure 3:
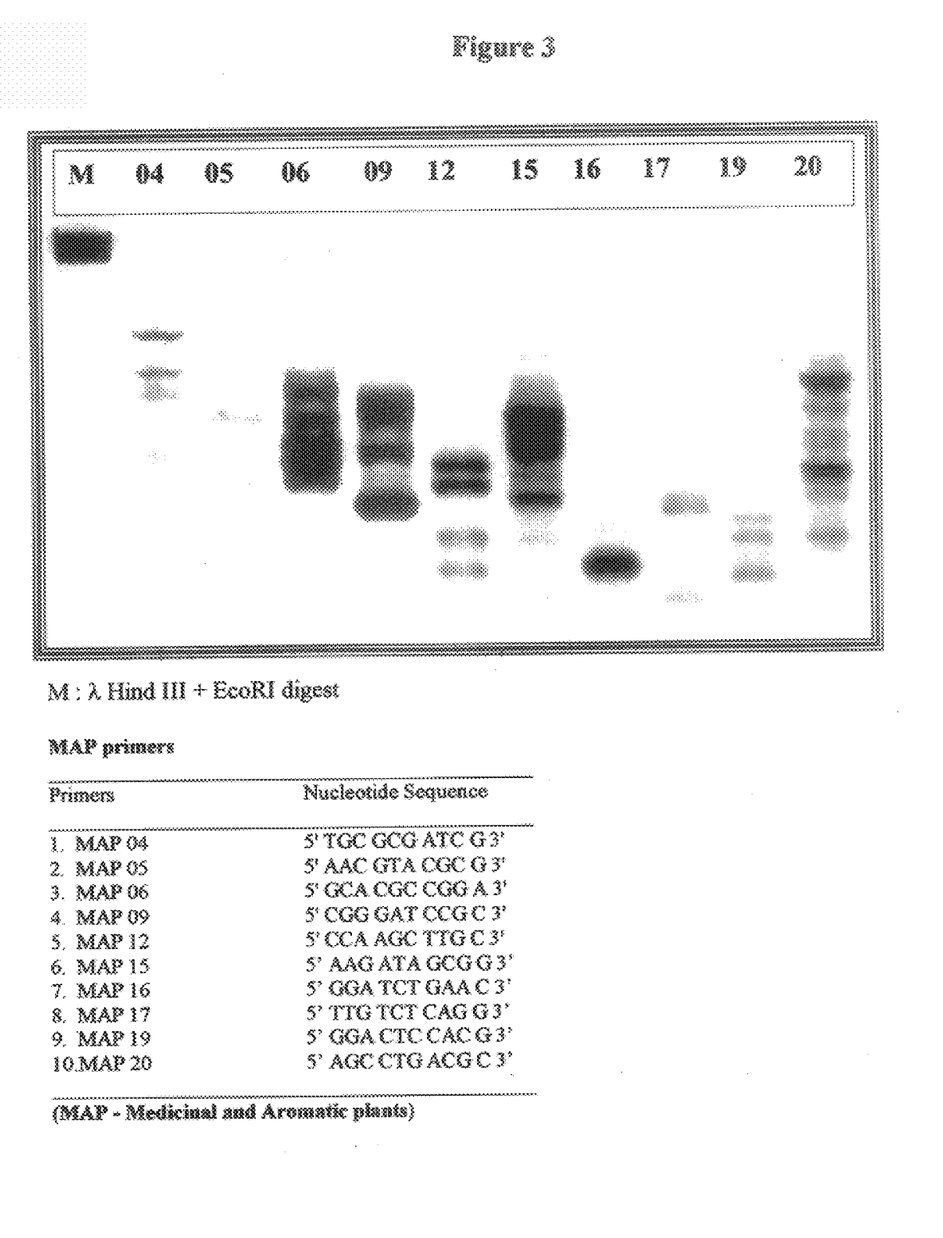
FIG. 3 shows a typical RAPD profile of the Streptomyces CIMAP-$A_1$ strain. The sequences of the primers MAP04, MAP05, MAP06, MAP09, MAP12, MAP15, MAP16, MAP 17, MAP19, and MAP20 (SEQ ID NOs: 1–10, respectively) are given.
Figure 4:
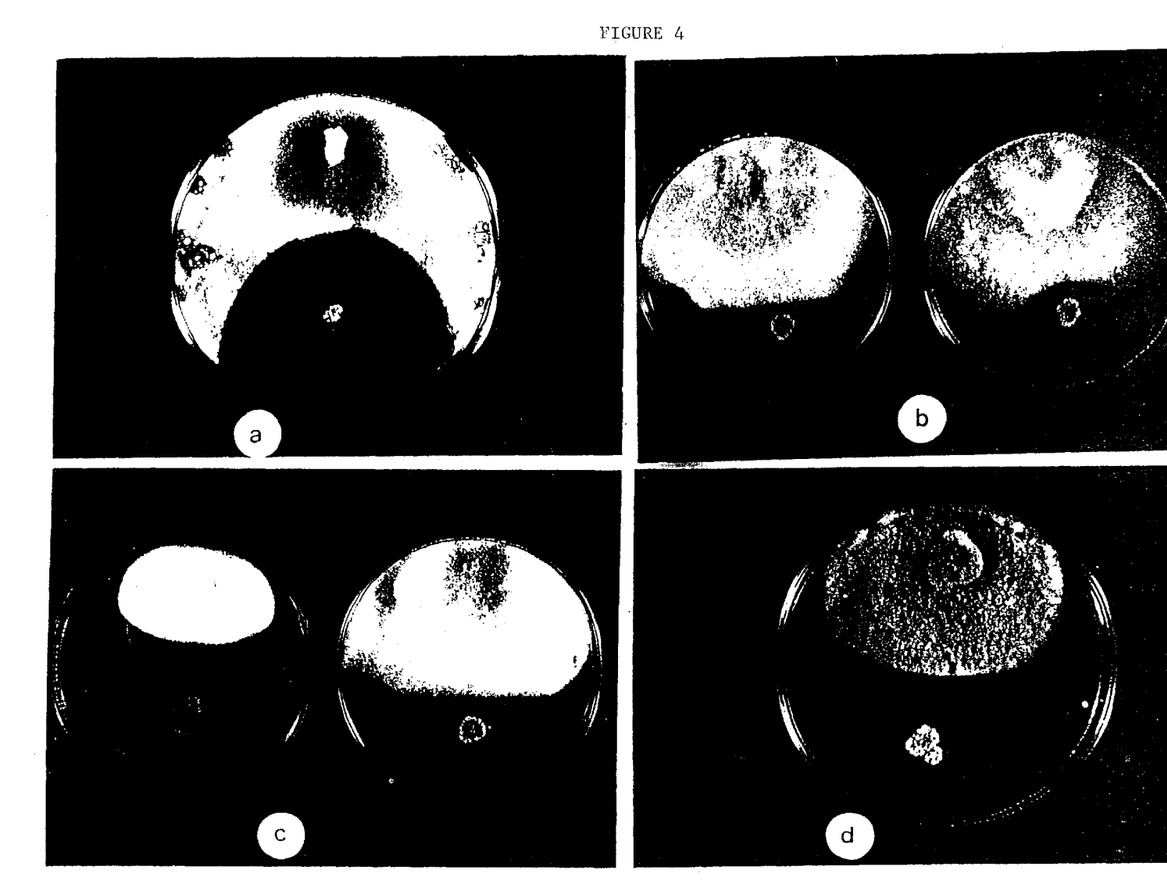
Figure 5:
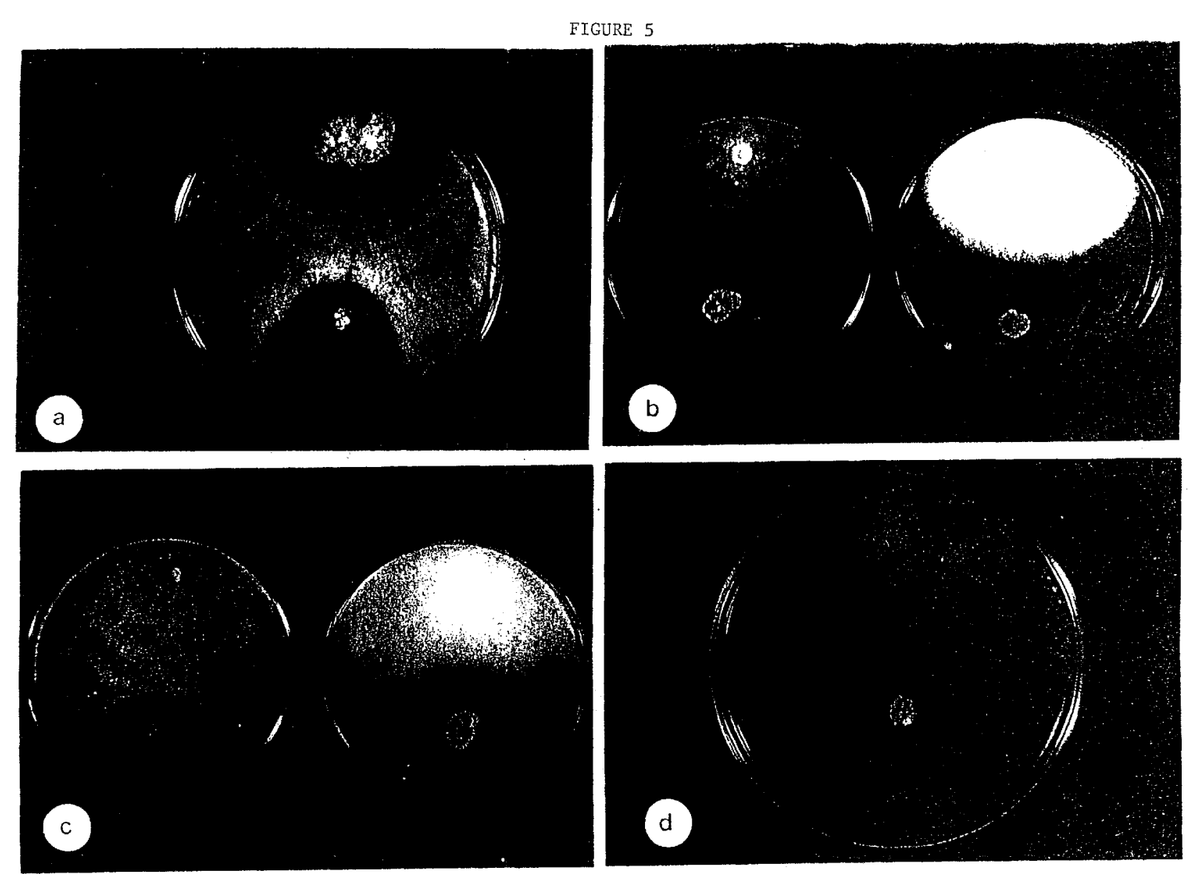

Still another embodiment of the invention provides a novel strain having the following characteristics:
  a) producing smooth, dull white colonies on Poison Disk Assay (PDA) which later forms discrete and lichonoid colonies,
  b) in late stages of growth, the present strain produces white aerial mycelium which later turn into dark brown in color,
  c) aerial mycelium at maturity form chain of spores, and
  d) exhibiting unique fingerprint pattern as shown in FIG. 3.

Still another embodiment of the present invention provides a strain Streptomyces CIMAP-$A_1$ having highly effective growth inhibiting properties against *Sclerotinia sclerotiorum* by 90%, *Curvularia andropogonis* by 85%, *Alternaria phragmospora* by 66% and *Colletotrichun acutatum* by 60%.

Yet another embodiment of the present invention provides a culture (CIMAP-$A_1$) which exhibits photopathogenic activity against the Phytopathogenic species selected from the group comprising Rhizoctonia, Sclerotinia, Pythium, Fusarium, Curvularia, Alternaria, Collectotrichum and Thielavia.

One more embodiment of the present invention provides a method for evaluating antifungal activity of CIMAP-A1 vitro against wide range of phytopathagenic fungi of medicinal and aromatic plants.

BRIEF DESCRIPTION OF ACCOMPANYING DRAWINGS

The patent or patent application file contains at least one drawing executed in color. Copies of this patent or patent application publication with color drawing(s) will be provided by the Office upon request and payment of the necessary fee.

In the accompanying drawings,

FIGS. 4($a$) to ($d$). shows in vitro inhibition in plate I by the Streptomyces CIMAP-$A_1$ strain of phytopathogenic fungi. (a) *Sclerotinia sclerotiorum,* (b) *Fusarium semitectum* & *F. moniliformei,* (c) *Thielavia basicola* & *F. semitectum* (Opium poppy) and (d) *corynespora cassiicola.*

FIGS. 5($a$) to ($d$). shows in vitro inhibition of the following pathogenic fungi in plate II by the Streptomyces CIMAP-$A_1$ strain: (a) *Rhizoctonia solani* (Opium poppy), (b) *Colletotrichum acutatum* & *Fusarium moniliforme,* (c) *R. solani* (salvia) & *Pythium dissotocum* and (d) *Alternaria alternata.*

MATERIAL AND METHODS

Isolation of Streptomyces sp. from Soil

Soil samples were collected randomly from the CIMAP experimental fields at Lucknow to a depth of 0–2-cm, mixed thoroughly and stored at 5° C. in polythene bag. One gram soil samples were dissolved in 10 ml sterile distilled water (SDW) and further diluted to 1/100, 1/200, 1/500 and 1/1000 with SDW and stirred vigrously to obtain homogenous spores suspension. An aliquot of 0.5 ml of different dilutions was inoculated and spread over Nutrient Agar/Potato-Dextrose Agar plates which were incubated at 25±1° C. in dark for 3–5 days. The discrete and lichonoid colonies appearing to be Streptomyces sp. were subcultured on fresh PDA plants. The cultures were later purified by single spore isolation technique and maintained onto PDA slants under mineral oil at 25° C.

Bacterial Growth Media

All bacterial growth media were prepared using distilled water and sterilized by autoclaving prior to use. All bacterial samples were handled using standard aseptic laboratory techniques to maintain purity.

PDA (Potato-Dextrose-Agar): Potato infusion (200 g/l), dextrose (20 g/l and agar 18 g/l. This medium is available commercially from Hi-Media Laboratory, Difco Co. Potato Dextrose Broth(PDB) was made in the same manner except that agar was omitted.

NA (Nutrient Agar) medium: 3 g/l beef extract, 5 g/l peptic digest of animal tissue and 1.5 g/l agar (HI-Media Laboratory Bombay. India) in distilled water. (pH 6.8).

Delivery medium: The delivery medium comprising Sand/Soil/Corn meal (6:3:1) was moistened with water and was sterilized by steam sterilization prior to use. Sterilization was typically performed by autoclaving twice, each time for 60 minutes.

Harvesting of Bacterial Growth

For mycelial growth of strain Streptomyces CIMAP $A_1$, 500 ml Potato-Dextrose Broth (PDB) 500 ml Erlenmayer flasks were inoculated with 100 ml of stock culture and incubated on shaker with a speed 200 rpm at 25° C. for three days. Mycelia were harvested by centrifugation at 500 rpm for 10 minutes. Supernatant then decanted off and the concentrated suspension of mycelia and spores was used directly to inoculate delivery medium in the ratio of 1:10, 1:20, 1:50; 1:100. Spores of strain Streptomyces CIMAP-$A_1$ was also produced by growing culture for 7–10 days on solid medium (for example on PDA) Mycelia and spores were harvested from culture in Petri dishes by scrapping the surface of the agar into distilled water. The suspension of spores and mycelia in water was mixed directly into the delivery medium.

Fungal Pathogens

The cultures of fungal pathogens were obtained from the infected tissues of various medicinal and aromatic plants as listed in Table-1. The were maintained onto Potato-Dextrose-Agar or Corn meal-Agar slants under mineral oil at 20° C. in the culture collection of Department of Microbiology and Plant Pathology, CIMAP, Lucknow, India. Pathogenicity of each of the cultures was established on host the under glasshouse conditions.

Characterization of the Isolate of Streptomyces

The isolates of Streptomyces were grown on PDA and their growth characteristics (both cultural and morphological) were observed as per standardized procedure described by Shirling and Gottlib 1968, International Journal of Systematic Bacteriology 18: 69–186). The isolate Streptomyces CIMAP-$A_1$ initially produce smooth and dull white colonies on PDA which later form discrete and lichnoid colonies. In the later stages of growth it produces a weft white of aerial mycelium and turn into dark brown in color. The aerial mycelium at maturity form chain of spores called orthrospores.

DNA Isolation and PCR Amplification Reactions

DNA was isolated from the fungus essentially according to the protocol (Khanuja et al, 1999 Plant Molecular Biology Reporter, 17: 74). Polymerase chain reactions (PCRs) were carried out in 25$\mu$ volume. A reaction tube contained 25 $\mu$g of DNA, 0.2 unit of Taq DNA polymerase, 100 $\mu$M each of dNTPs, 1.5 mM $MgCl_2$ and 5 p mol of decanucleotide Primers. The amplifications were carried out using the DNA. Engine thermal cycler (MJ Research, USA) following the protocol of Shasany et al. 1998, Journal of Biosciences 23: 641–646). The amplified products were loaded in 1.2% agarose gel containing 0.5 $\mu$g $ml^{-1}$ of ethidium bromide and photographed by Image Master VDS system. Ten random decamer primers synthesized in the laboratory were used to prepare the fingerprint pattern of the fungs. The pattern (FIG. 3) was found to be unique incomparison with other microorganisms especially Streptomyces spp.

The invention is described in detail herein below with reference to the accompanying drawings and following examples which are provided merely to illustrate the invention and should not be construed as limitations on the inventive concept.

EXAMPLES

In vitro Testing of Antagonistic Activity of Strain Streptomyces CIMAP-$A_1$

The antagonistic activity of strain Streptomyces CIMAP-$A_1$ was tested in vitro by following common dual cultures technique on PDA (Morton D T and N. H. Stroube 1955, Phytopathology 45: 419–420) where inhibition zones in between the colonies of antagonist and pathogen was measured 6 days after inoculation and percent growth inhibition was determined as shown in table 1 and FIGS. 1 and 2. The newly isolated sdtrain of Streptomyces, Streptomyces CIMAP-$A_1$, was able to inhibit growth of Stremphyllum sp. and botrytis cincrea by 90%, *Selerotinia sclerotiorum* by 85%, Curvularia spp. By 80–85%, Alternaria spp by 66–67%, *Corynespora cassiicola* by 64%, *Ihielavia basicola* by 54% *Rhizoctorion solain* by 20–28% Pythium spp. By 8–20% and Fusarium spp. By 20–28 in vitro (Table 1).

In vivo Testing of the Streptomyces CIMAP $A_1$ on Different Known Pathogens

Opium poppy seeds were treated with the strain of Streptomyces CIMAP-$A_1$ of the present invention and exposed to the fungal pathogen, *P. dissotocum* causing pre-emergence damping-off disease and maximum emergence of seedlings were observed which also show growth characteristic similar to the untreated unexposed control plants. Seeds treated with Streptomyces CIMAP-$A_1$ and exposed to the inoculum of fungal pathogen also produced plants showing growth characteristics superior to the untreated, unexposed plants.

The spray of cell free culture filtrate of Streptomyces CIMAP-$A_1$ on the foliage of a geranium in the commercial fields significantly reduced by fungal infection caused by *Colletotrichum acutatum.* The strain Streptomyces CIMAP-$A_1$ of the present invention produce vegetative cells or spores for incorporation into a delivery medium. The composition comprising the vegetative cells and spores of Streptomyces CIMAP-$A_1$ and the delivery medium has a long shelf life and is suitable for delivering the antagonisdt to plants for effective control of fungal phytopathogens.

ADVANTAGES

Streptomyces CIMAP-$A_1$ strain is capable of inhibiting the growth of wide range of phytopathogenic fungi including Rhizoctonia, Sclerotinia, Pythium, Fusarium, Curvularia, and Alternaria which have been causing various kinds of diseases on agricultural as well as horticultural crops. A thorough perusal of review of literature reveals that no such strain of Streptomyces has been obtained. The Streptomyces CIMAP $A_1$ strain has moreover novelty in showing growth inhibition of dark spored pathogenic fungi which are cosmopolitan in distribution. Therefore, it can be utilized as biocontrol agent against several plant pathogenic fungi of agricultural crops. This new strain multiplies on simple delivery medium and is cost effective and can be exploited commercially. It is non hazardous and ecofriendly in nature.

TABLE 1

In vitro growth inhibition of fungal phytopathogens of some important medicinal & aromatic plants by the new strain Streptomyces-CIMAP-$A_1$

| S. No. | Pathogens | Disease | Host | Inhibition (%) |
|---|---|---|---|---|
| 1. | *Alternaria alternata* | Leaf blight | Menthol Mint | 67.00 |
| 2. | *A. phragmospora* | " | Opium poppy | 66.00 |

TABLE 1-continued

In vitro growth inhibition of fungal phytopathogens of some important medicinal & aromatic plants by the new strain Streptomyces-CIMAP-A$_1$

| S. No. | Pathogens | Disease | Host | Inhibition (%) |
|---|---|---|---|---|
| 3. | *Botrytis cineria* | Twig blight | Plumbago | 90.00 |
| 4. | *Collectotrichum acutatum* | Anthracnose | Geranium | 60.00 |
| 5. | *C. gloeosporioides* | " | " | 62.00 |
| 6. | *Corynespora cassiicola* | Leaf blight | " | 64.00 |
| 7. | *Curvularia andropogonis* | Leaf blight | Java citronella | 85.00 |
| 8. | *C. trifolii* | " | Lemon grass | 80.00 |
| 9. | *Fusarium moniliforme* | Collor rot | Java citronella | 20.00 |
| 10. | *F. semitectum* | Wilt | Menthol mint | 12.00 |
| 11. | *F. oxysporum* | " | " | 28.00 |
| 12. | *Pythium aphanidermatum* | Lethal yellowing | Java citronella | 08.00 |
| 13. | *P. dissotocum* | Damping off | Opium poppy | 20.00 |
| 14. | *Rhizopus stolonifer* | Stem rot | Periwinkle | 10.00 |
| 15. | *Rhizoctonia solani* | Collar rot | Opium poppy | 20.00 |
| 16. | " | Wilt | Geranium | 28.50 |
| 17. | " | Wilt | Psyllium | 24.00 |
| 18. | " | Wilt | Artemisia | 21.00 |
| 19. | *Stemphyllium sp.* | Leaf spot | Menthol mint | 90.00 |
| 20. | *Sclerotinia sclerotiorum* | Stem rot | Psyllium | 85.00 |
| 21. | *Thielavia basicola* | Stolon rot | Menthol mint | 54.00 |

What is claimed is:

1. A biologically pure culture of Streptomyces sp. CIMAP A$_1$ strain bearing ATCC Accession No. PTA-4131 and capable of inhibiting the growth of phytopathogenic fungi.

2. A strain as claimed in claim 1 having the following characteristics:
   (a) producing smooth, dull white colonies on Poison Disk Assay (PDA) which later forms discrete and lichonoid colonies,
   (b) in late stages of growth, the present strain produces white aerial mycelium which later turn into dark brown in color,
   (c) aerial mycelium at maturity form chain of spores, and
   (d) exhibiting unique fingerprint pattern as shown in FIG. 3.

3. A culture as claimed in claim 1 exhibiting photopathogenic activity against Phytopathogenic species selected from the group consisting of Rhizoctonia, Sclerotinia, Pythium, Fusarium, Curvularia, Alternaria, Collectotrichum and Thielavia.

4. A strain Streptomyces CIMAP-A$_1$ as claimed in claim 1, which inhibits the growth of *Sclerotinia sclerotiorum* by at least 90%, *Curvularia andropogonis* by at least 85%, *Alternaria phragmospora* by at least 66% and *Colletotrichun acutatum* by at least 60%.

* * * * *

SEQUENCE LISTING

<160> NUMBER OF SEQ ID NOS: 10

<210> SEQ ID NO 1
<211> LENGTH: 10
<212> TYPE: DNA
<213> ORGANISM: Artificial sequence
<220> FEATURE:
<223> OTHER INFORMATION: primer

<400> SEQUENCE: 1
tgcgcgatcg    10

<210> SEQ ID NO 2
<211> LENGTH: 10
<212> TYPE: DNA
<213> ORGANISM: Artificial sequence
<220> FEATURE:
<223> OTHER INFORMATION: primer

<400> SEQUENCE: 2
aacgtacgcg    10

<210> SEQ ID NO 3
<211> LENGTH: 10
<212> TYPE: DNA
<213> ORGANISM: Artificial sequence
<220> FEATURE:
<223> OTHER INFORMATION: primer

<400> SEQUENCE: 3
gcacgccgga    10

<210> SEQ ID NO 4
<211> LENGTH: 10
<212> TYPE: DNA
<213> ORGANISM: Artificial sequence
<220> FEATURE:
<223> OTHER INFORMATION: primer -continued

```
<400> SEQUENCE: 4
cgggatccgc                                                          10

<210> SEQ ID NO 5
<211> LENGTH: 10
<212> TYPE: DNA
<213> ORGANISM: Artificial sequence
<220> FEATURE:
<223> OTHER INFORMATION: primer

<400> SEQUENCE: 5
ccaagcttgc                                                          10

<210> SEQ ID NO 6
<211> LENGTH: 10
<212> TYPE: DNA
<213> ORGANISM: Artificial sequence
<220> FEATURE:
<223> OTHER INFORMATION: primer

<400> SEQUENCE: 6
aagatagcgg                                                          10

<210> SEQ ID NO 7
<211> LENGTH: 10
<212> TYPE: DNA
<213> ORGANISM: Artificial sequence
<220> FEATURE:
<223> OTHER INFORMATION: primer

<400> SEQUENCE: 7
ggatctgaac                                                          10

<210> SEQ ID NO 8
<211> LENGTH: 10
<212> TYPE: DNA
<213> ORGANISM: Artificial sequence
<220> FEATURE:
<223> OTHER INFORMATION: primer

<400> SEQUENCE: 8
ttgtctcagg                                                          10

<210> SEQ ID NO 9
<211> LENGTH: 10
<212> TYPE: DNA
<213> ORGANISM: Artificial sequence
<220> FEATURE:
<223> OTHER INFORMATION: primer

<400> SEQUENCE: 9
ggactccacg                                                          10

<210> SEQ ID NO 10
<211> LENGTH: 10
<212> TYPE: DNA
```

```
<213> ORGANISM: Artificial sequence
<220> FEATURE:
<223> OTHER INFORMATION: primer

<400> SEQUENCE: 10
agcctgacgc                                                          10
```